United States Patent
Lipinski et al.

(10) Patent No.: US 10,881,596 B2
(45) Date of Patent: Jan. 5, 2021

(54) COSMETIC COMPOSITION FOR ENHANCING PROPERTIES OF PRE-COLORED KERATIN FIBERS

(71) Applicant: KAO GERMANY GMBH, Darmstadt (DE)

(72) Inventors: Normen Lipinski, Darmstadt (DE); Andreas Picker, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 0 days.

(21) Appl. No.: 16/466,367

(22) PCT Filed: Dec. 1, 2017

(86) PCT No.: PCT/EP2017/081151
§ 371 (c)(1),
(2) Date: Jun. 4, 2019

(87) PCT Pub. No.: WO2018/104165
PCT Pub. Date: Jun. 14, 2018

(65) Prior Publication Data
US 2020/0078285 A1    Mar. 12, 2020

(30) Foreign Application Priority Data
Dec. 5, 2016 (EP) .................... 16202181

(51) Int. Cl.
*A61Q 5/10* (2006.01)
*A61K 8/49* (2006.01)
*A61K 8/06* (2006.01)
*A61K 8/64* (2006.01)
*A61K 8/891* (2006.01)
*A61K 8/898* (2006.01)

(52) U.S. Cl.
CPC ............ *A61K 8/4913* (2013.01); *A61K 8/068* (2013.01); *A61K 8/64* (2013.01); *A61K 8/891* (2013.01); *A61K 8/898* (2013.01); *A61Q 5/10* (2013.01)

(58) Field of Classification Search
CPC .... A61K 2800/59; A61K 8/891; A61K 8/898; A61K 8/4913; A61K 8/64; A61K 8/68; A61Q 5/10; A61Q 5/12
See application file for complete search history.

(56) References Cited

U.S. PATENT DOCUMENTS

2011/0293551 A1*  12/2011  Molenda .................. A61K 8/06
                                                      424/70.9
2013/0189198 A1*  7/2013  Tamareselvy .......... A61K 8/463
                                                      424/49

FOREIGN PATENT DOCUMENTS

| EP | 2 090 291 A1 | 8/2009 |
|---|---|---|
| EP | 2 090 295 A1 | 8/2009 |
| EP | 2 186 543 A1 | 5/2010 |
| WO | 2014199936 A1 * | 12/2014 |
| WO | WO 2014199936 A1 * | 12/2014 |

OTHER PUBLICATIONS

KCC Beauty, title: SeraShine® EM 322C; product information version 2.0. Date of revision Oct. 2017. (Year: 2017).*
Author: Melissa Conrad Stöppler; title: Medical Definition of Gliadin, downloaded from https://www.medicinenet.com/script/main/art.asp?articlekey=11381 on Mar. 23, 2020. (Year: 2020).*
International Search Report dated Jan. 10, 2018.

* cited by examiner

*Primary Examiner* — Yanzhi Zhang
(74) *Attorney, Agent, or Firm* — Norris McLaughlin, P.A.

(57) ABSTRACT

The present invention is on a cosmetic composition for improving color brilliance and wash fastness of artificially-colored keratin fibers. The effect is achieved by the combination of pyrrolidone carboxylic acid esters, pyrrolidone carboxylic acid and/or its salts, and amodimethicone microemulsion. A process for treating keratin fibers, a use of the composition and well as a kit-of-parts is disclosed.

13 Claims, No Drawings

COSMETIC COMPOSITION FOR ENHANCING PROPERTIES OF PRE-COLORED KERATIN FIBERS

This application is the U.S. National Stage of International Application No. PCT/EP2017/081151, filed Dec. 1, 2017, which claims foreign priority benefit under 35 U.S.C. § 119 of European Application No. 16202181.0 filed Dec. 5, 2016 the disclosures of which are incorporated herein by reference.

The present invention relates to a cosmetic composition for enhancing properties of pre-colored keratin fibers, in terms of color brilliance, shine, and wash fastness. Moreover, a process and use are disclosed.

Since human beings have started to think about beauty and their outward appearance, healthy and especially shiny and brilliant hair was a sign of well-being, comfort, luxuriousness and wealthiness. This trend has continued until today and can still be seen in current market portfolios of hair care producers as more and more products appear suggesting delivery of enhanced optical properties of keratinous fibers. On colored hair additional benefits, besides cleansing and/or conditioning, such as color protection over several hair washes are demanded by customers.

Different approaches have been selected to enhance color protection on artificially colored hair. A well-known compound class is pyrrolidone carboxylic acid esters which exhibit a beneficial effect on human hair (EP 2090291). There are several market products available which make use of this compound class in combination with silicones (Mintel 4124145, 3570147), glycoproteins (Mintel 2800827), or a combination of glycoproteins and silicones (Mintel 3800209). Compositions comprising glycoproteins and silicones without pyrrolidone carboxylic acid esters (Mintel 4124145) are known as well.

Although the aforementioned products serve their purpose well, there still is the consumers wish for a better product performance in terms of color brilliance and shine on artificially colored hair combined with improved wash fastness.

Based on the teachings of the prior art, the inventors unexpectedly found that the combination of pyrrolidone carboxylic acid esters, pyrrolidone carboxylic acid, and an amodimethicone microemulsion provided superior benefits on artificially colored hair, in particular in terms of color brilliance and wash fastness on undamaged and, especially, damaged hair.

Therefore, the first object of the present invention is an aqueous cosmetic composition comprising:
  a) one or more compound(s) according to the general structure of

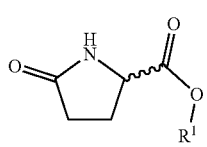

Formula I

Wherein $R^1$ is selected from straight, saturated or unsaturated alkyl chain with $C_1$ to $C_{22}$, or branched, saturated or unsaturated alkyl chain with $C_3$ to $C_{22}$, phenyl alkoxy group with an alkyl chain length of $C_1$ to $C_4$, and/or phenoxy alkyl group with an alkyl chain of $C_1$ to $C_4$, and wherein the proline moiety has either D and/or L configuration, b) pyrrolidone carboxylic acid and/or its salt,
  c) amodimethicone, wherein amodimethicone is added to the composition as microemulsion.

The second object of the present invention is the use of the composition as defined above for improving wash fastness of artificially colored keratin fibers, preferably human keratin fibers, more preferably human hair.

The third object of the present invention is the use of the composition as defined above for enhancing color brilliance and shine of artificially colored keratin fibers, preferably human keratin fibers, more preferably human hair.

The fourth object of the present invention is a process for maintaining color brilliance and shine, and improving wash fastness of artificially colored keratin fibers, preferably human keratin fibers, more preferably human hair, comprising the steps of:
  a) optionally wetting and/or cleansing the hair,
  b) applying the composition as defined above and massaging it into keratin fibers for 10 s to 600 s,
  c) optionally rinsing off the composition,
  d) optionally drying the hair.

As the composition according to the present invention may be a cleansing and/or conditioning composition, components of the composition may be subsequently applied onto hair.

The composition of the present invention comprises at least one pyrrolidone carboxylic acid ester according to formula I. The alkyl chain length, in the preferred form, is between $C_8$ and $C_{20}$, more preferably between $C_{12}$ and $C_{20}$, and most preferably between $C_{14}$ and $C_{20}$. Suitable pyrrolidone carboxylic acid esters are with the alkyl chain of methyl, ethyl, n-propyl, isopropyl, n-butyl, isobutyl, n-hexyl, n-octyl, n-nonyl, n-decyl, ethylhexyl, methylhexyl, lauryl, myristyl, cetyl, octyldodecyl, isostearyl, stearyl, arachidyl, behenyl, oleyl, linoleyl, benzyl, phenoxyethyl. Preferred are n-octyl, n-nonyl, n-decyl, ethylhexyl, methylhexyl, capryl, lauryl, myristyl, cetyl, octyldodecyl, stearyl, isostearyl, arachidyl, behenyl, oleyl and linoleyl. More preferred are lauryl, myristyl, cetyl, octyldodecyl, stearyl, isostearyl, arachidyl, behenyl, oleyl, and linoleyl. The particularly preferred pyrrolidone carboxylic acid ester is octyldodecyl pyrrolidone carboxylic acid which is available under the trade name Sebumol ODPC offered by Zschimmer & Schwarz Ltd.

The total concentration of pyrrolidone carboxylic acid esters in the composition is in the range of 0.001% to 5% by weight, preferably in the range of 0.002% to 2% by weight, more preferably in the range of 0.004% to 1% by weight, and most preferably 0.004% to 0.5% by weight, calculated to the total of the composition.

The composition comprises pyrrolidone carboxylic acid and/or its salts. In principle, any pyrrolidone carboxylic acid salt is suitable. Examples are aluminium, calcium, copper, magnesium, potassium, sodium and zinc salts. Particularly preferred salts are potassium and sodium salts. The most preferred salt is the sodium salt. Sodium pyrrolidone carboxylate is available under the trade name Protelan PCA 40 from Zschimmer & Schwarz Ltd.

The total concentration of pyrrolidone carboxylic acid and/or its salts is in the range of 0.001% to 5% by weight, preferably in the range of 0.002% to 2% by weight, more preferably in the range of 0.004% to 1% by weight, and most preferably in the range of 0.004% to 0.5% by weight.

In a preferred embodiment of the present invention the weight ratio of the pyrrolidone carboxylic acid esters to pyrrolidone carboxylic acid and/or its salts is in the range of 0.1 to 100, preferably in the range of 0.5 to 50, more preferably in the range of 1 to 20, and most preferably in the range of 1 to 10.

The composition further comprises aminated silicones which are added in the form of a microemulsion. The term microemulsion within the meaning of the present invention is to be understood as an emulsion with a droplet size in the range of 50 nm to 1000 nm.

Suitable aminosilicone microemulsions are offered by Wacker Corp. under the trade names Wacker Belsil, in particular Wacker Belsil ADM 6057 and Wacker Belsil ADM 8020 VP. Further microemulsions are offered by Shin-Etsu Corp. under the trade name X-52-2265, and DC CE 8170 AF by Dow Corning Corp.

The preferred microemulsion is X-52-2265 from Shin-Etsu Corp and DC CE 8170 AF by Dow Corning Corp. The particularly preferred microemulsion is DC CE 8170 AF.

The composition comprises amodimethicone which is added as a microemulsion at a total concentration in the range of 0.001% to 1% by weight, preferably 0.002% to 0.5% by weight, more preferably 0.0025% to 0.2% by weight, calculated as active amodimethicone matter to the total of the composition.

The composition may further comprise glycoproteins. In principle any source of glycoproteins is suitable. Examples are glycoproteins derived from milk, serum, cell hydrolyzates, and/or hydrolyzates of extracellular matrix. As the skilled reader will notice, the proteins may or may not be fully or partially hydrolyzed. The term 'hydrolyzed' is to be understood as a process that breaks glycoproteins into peptides. In general, glycoproteins and/or their hydrolyzation products may possess a molecular weight of 1,000 Da to 50,000 Da, more preferably from 5,000 Da 30,000 Da, most preferably from 10,000 to 20,000 Da. The proteins and/or their hydrolyzates may be further chemically modified such as by attachment of quaternary ammonium salts.

Suitable examples of glycoproteins are of yeast origin and marketed under the tradename Musol 20 ECT. Further suitable glycoproteins and/or their hydrolyzates are offered as 'milk protein concentrate', 'Lactofil' is offered by Gattefossé Corp., 'Milkpro' is offered by IKEDA Corp., and 'Milk-Amino 20' by Lonza Corp.

The total concentration of glycoproteins and/or their hydrolyzates in the composition is in the range of 0.001% to 2% by weight, preferably in the range of 0.02% to 1% by weight, and more preferably in the range of 0.0025% to 0.5% by weight, calculated as dry matter to the total of the composition.

The composition may comprise cationic, anionic, zwitterionic, amphoteric, and/or non-ionic surfactants. In a preferred embodiment of the present invention, the composition comprises at least one non-ionic surfactants, at least two anionic surfactants, and at least one amphoteric surfactant.

Suitable nonionic surfactants are alkyl polyglycosides according to the general structure:

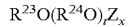

Wherein Z denotes a reducing carbohydrate with $C_5$ to $C_6$, $R^{23}$ is an alkyl group with $C_8$ to $C_{18}$, $R^{24}$ is ethyl or propyl, t ranges from 0 to 10, and x ranges from 1 to 5. Suitable compounds according to this structure are $C_9$-$C_{11}$ alkylpolyglycoside, the structures disclosed in EP-A 70 074, and JP 2015-123019A.

The preferred compound according to the structure of above is decyl glucoside.

Suitable non-ionic surfactants are in general all commonly known non-ionic surfactants available on the market.

Suitable examples for non-ionic surfactants are fatty alcohol ethoxylates of the following general structure

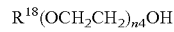

wherein $R^{18}$ is straight or branched, saturated or unsaturated alkyl chain which may be synthetic or natural with a C chain length in the range of 8 to 40, preferably 9 to 30 and more preferably 9 to 24 and n4 is a number in the range of 5 to 40, preferably 9 to 30.

Non-limiting suitable examples of the fatty alcohol ethoxylates are C9-11 Pareth-6, C9-11 Pareth-8, C9-15 Pareth-8, C11-13 Pareth-9, C11-13 Pareth-10, C11-15 Pareth-5, C11-15 Pareth-7, C11-15 Pareth-9, C11-15 Pareth-12, C11-15 Pareth-15, C11-15 Pareth-20, C11-15 Pareth-30, C11-15 Pareth-40, C11-21 Pareth-10, C12-13 Pareth-5, C12-13 Pareth-6, C12-13 Pareth-7, C12-13 Pareth-9, C12-13 Pareth-10, C12-13 Pareth-15, C12-13 Pareth-23, C12-14 Pareth-5, C12-14 Pareth-7, C12-14 Pareth-9, C12-14 Pareth-11, C12-14 Pareth-12, C12-15 Pareth-5, C12-15 Pareth-7, C12-15 Pareth-9, C12-15 Pareth-10, C12-15 Pareth-11, C12-15 Pareth-12, C12-16 Pareth-5, C12-16 Pareth-7, C12-16 Pareth-9, C13-15 Pareth-21, C14-15 Pareth-7, C14-15 Pareth-8, C14-15 Pareth-11, C14-15 Pareth-12, C14-15 Pareth-13, C20-22 Pareth-30, C20-40 Pareth-10, C20-40 Pareth-24, C20-40 Pareth-40, C20-40 Pareth-95, C22-24 Pareth-33, Beheneth-5, Beheneth-10, Beheneth-15, Beheneth-20, Beheneth-25, Beheneth-30, Ceteareth-5, Ceteareth-6, Ceteareth-7, Ceteareth-10, Ceteareth-11, Ceteareth-12, Ceteareth-15, Ceteareth-20, Ceteareth-25, Ceteareth-30, Ceteareth-35, Ceteareth-40, Laureth-5, Laureth-10, Laureth-15, Laureth-20, Laureth-25, Laureth-30, Laureth-40, Myreth-5, Myreth-10, Ceteth-5, Ceteth-10, Ceteth-15, Ceteth-20, Ceteth-25, Ceteth-30, Ceteth-40, Oleth-5, Oleth-10, Oleth-15, Oleth-20, Oleth-25, Oleth-30, Oleth-40, Steareth-5, Steareth-10, Steareth-15, Steareth-20, Steareth-25, Steareth-30, Steareth-35, and Steareth-40. They may also be comprised in the compositions as a mixture of more than one surfactant.

Further suitable nonionic surfactants are polypropylene glycol ethers of fatty alcohol according to general structure

wherein $R^{19}$ is straight or branched, saturated or unsaturated fatty alcohol which may be synthetic or natural with a C chain length in the range of 8 to 40, preferably 9 to 30 and more preferably 9 to 24 and n5 is a number in the range of 1 to 40, preferably 3 to 30.

Suitable non-limiting examples are PPG-3 Caprylyl ether, PPG-5 Caprylyl ether, PPG-10 Caprylyl ether, PPG-10 Cetyl ether, PPG-20 Cetyl ether, PPG-28 Cetyl ether, PPG-30 Cetyl ether, PPG-7 Lauryl ether, PPG-10 Lauryl ether, PPG-10 Oleyl ether, PPG-20 Oleyl ether, PPG-23 Oleyl ether, PPG-30 Oleyl ether, PPG-11 Stearyl ether and PPG-15 Stearyl ether.

Further suitable nonionic surfactants are polyethylene glycol fatty acid esters of the following general structure

wherein $R^{20}$ is straight or branched, saturated or unsaturated alkyl group which may be synthetic or natural with a C chain length in the range of 7 to 39, preferably 9 to 29 and more preferably 9 to 23 and n6 is a number in the range of 5 to 40, preferably 9 to 30.

Suitable non-limiting examples are PEG-8 Behenate, PEG-8 Caprate, PEG-8 Caprylate, PEG-5 Cocoate, PEG-8 Cocoate, PEG-9 Cocoate, PEG-10 Cocoate, PEG-15 Cocoate, PEG-6 Isopalmitate, PEG-6 Isostearate, PEG-8

Isostearate, PEG-9 Isostearate, PEG-10 Isostearate, PEG-12 Isostearate, PEG-20 Isostearate, PEG-30 Isostearate, PEG-40 Isostearate, PEG-6 Laurate, PEG-8 Laurate, PEG-9 Laurate, PEG-10 Laurate, PEG-12 Laurate, PEG-14 Laurate, PEG-20 Laurate, PEG-30 Laurate, PEG-8 Myristate, PEG-20 Myristate, PEG-5 Oleate, PEG-6 Oleate, PEG-7 Oleate, PEG-8 Oleate, PEG-9 Oleate, PEG-10 Oleate, PEG-11 Oleate, PEG-12 Oleate, PEG-15 Oleate, PEG-20 Oleate, PEG-30 Oleate, PEG-32 Oleate, PEG-6 Palmitate, PEG-18 Palmitate, PEG-20 Palmitate, PEG-5 Stearate, PEG-6 Stearate, PEG-7 Stearate, PEG-8 Stearate, PEG-9 Stearate, PEG-10 Stearate, PEG-12 Stearate, PEG-14 Stearate, PEG-15 Stearate, PEG-20 Stearate, PEG-25 Stearate, PEG-30 Stearate, PEG-35 Stearate and PEG-40 Stearate.

Further suitable nonionic surfactants are polypropylene glycol fatty acid esters of the following general structure

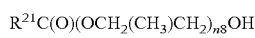

wherein $R^{21}$ is straight or branched, saturated or unsaturated alkyl group which may be synthetic or natural with a C chain length in the range of 7 to 39, preferably 9 to 29 and more preferably 9 to 23 and n8 is a number in the range of 1 to 40, preferably 9 to 30.

Suitable non-limiting examples are PPG-15 Isostearate, PPG-9 Laurate, PPG-26 Oleate and PPG-36 Oleate.

Further suitable nonionic surfactants are polyethylene glycol and polypropylene glycol ether of fatty alcohols of the following general structure

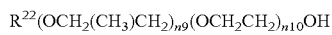

wherein $R^{22}$ is straight or branched, saturated or unsaturated alkyl group which may be synthetic or natural with a C chain length in the range of 7 to 39, preferably 9 to 29 and more preferably 9 to 23 and n9 and n10 may be the same or different and are a number in the range of 1 to 40.

Further suitable nonionic surfactants are ethoxylated triglycerides. Well known and commonly used examples are ethoxylated castor oil such as PEG-40 hydrogenated castor oil or and PEG-60 hydrogenated castor oil.

The composition may comprise non-ionic surfactant(s) at a total concentration from 0.01% to 2% by weight, preferably from 0.1% to 1.5% by weight, more preferably from 0.25% to 1% by weight, calculated to the total of the composition.

Suitable anionic surfactants are selected from compounds according to the structure

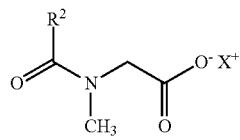

Formula II wherein $R^2$ is a straight or branched, substituted or unsubstituted, saturated or unsaturated alkyl chain with a carbon number of $C_9$ to $C_{21}$, preferably $R^2$ is a straight alkyl chain with a carbon number of $C_9$ to $C_{17}$, and $X^+$ is a cation selected from sodium, potassium, magnesium and ammonium ions, which are compounds based on the amino acid sarcosin which are commonly known as sarcosinates.

Suitable compounds are, for example, cocoyl sarcosinate and its salts, lauroyl sarcosinate and its salts, myristoyl sarcosinate and its salts, stearoyl sarcosinate and its salts, oleoyl sarcosinate and its salts, palmitoyl sarcosinate and its salts. Salts are formed with cations selected from sodium, potassium, magnesium, and ammonium ions.

The preferred first surfactant according to the structure of formula II is sodium lauroyl sarcosinate.

The total concentration of the surfactant according to formula II is in the range of 0.1% to 3.5% by weight, preferably 0.2% to 3.5% by weight, more preferably 0.5% to 3.5% by weight, calculated to the total of the composition.

Suitable second anionic surfactants are alkyl sulfate or preferably ethoxylated alkyl ether sulfate surfactant or mixtures thereof with an alkyl chain length of $C_{10}$ to $C_{22}$.

Suitable surfactants are laureth sulfates, coceth sulfate, pareth sulfate, capryleth sulphate, myreth sulfate, oleth sulfate, deceth sulfate, trideceth sulfate, coco sulphate, $C_{10}$-$C_{16}$ alkyl sulphate, $C_{11}$-$C_{15}$ alkyl sulphate, $C_{12}$-$C_{18}$ alkyl sulphate, $C_{12}$-$C_{15}$ alkyl sulphate, $C_{12}$-$C_{16}$ alkyl sulphate, $C_{12}$-$C_{13}$ alkyl sulfate, lauryl sulphate, myrystyl sulphate, palm kernel sulphate, cetearyl sulfate, cetyl sulphate, decyl sulphate, oleyl sulphate, behenyl sulphate and/or their salts. All of the aforementioned anionic surfactants may or may not be ethoxylated at various degrees.

Cations for the surfactants may be selected from sodium, potassium, magnesium and/or ammonium.

Suitable second anionic surfactant is sodium laureth sulfate with 1-5 ethylene oxide units.

The composition may comprise the second anionic surfactant at a total concentration in the range of 5% to 12.5% by weight, calculated to the total of the composition.

The amphoteric surfactant is selected from compounds according to the general structure(s) III and/or IV

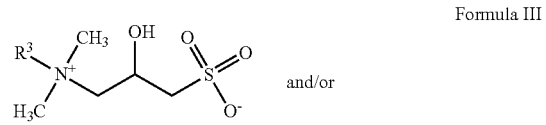

Formula III and/or

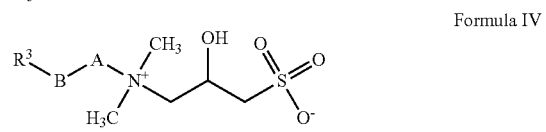

Formula IV wherein $R^3$ is a straight or branched, saturated or unsaturated, substituted or unsubstituted alkyl chain with a carbon number of $C_{10}$ to $C_{22}$, preferably $R^3$ is a straight alkyl chain with a carbon number of $C_{10}$ to $C_{16}$, A is a straight alkyl chain with a carbon number of $C_1$ to $C_6$ or a branched alkyl chain with a carbon number of $C_3$ to $C_6$, preferably A is a linear alkyl chain with a carbon number of $C_3$, and B is an amide or an ester group.

Suitable compounds are known as hydroxysultain surfactants, such as cocoamidopropyl hydroxysultaine, laurylamidopropyl hydroxysultaine, erucamidopropyl hydroxysultaine, lauryl hydroxysultaine, and cocoyl hydrodroxysultaine.

The preferred amphoteric surfactant is lauryl hydroxysultaine.

The composition may comprise amphoteric and/or zwitterionic surfactants at a total concentration in the range of 0.1% to 2%, preferably 0.25% to 1.75%, more preferably 0.5% to 1.5% by weight, calculated to the total of the composition.

The weight ratio of total anionic surfactant to total amphoteric surfactant in the composition is in the range from 2.55 to 155, preferably from 7.75 to 51, and more preferably from 9 to 25, and wherein the weight ratio of the first anionic surfactant to the second anionic surfactant is in the range of 0.008 to 0.6, preferably 0.02 to 0.6, and more preferably from 0.1 to 0.4.

The weight ratio of second anionic surfactant to amphoteric surfactant is in the range of 2.5 to 125, preferably from 3.0 to 100, more preferably from 3.5 to 50, further more preferably from 4 to 25.

The weight ratio of first anionic surfactant to amphoteric surfactant in the composition is in the range of 0.067 to 30, preferably from 0.13 to 12, more preferably from 0.13 to 4.

In a particular embodiment, the composition comprises as the first anionic surfactant sodium lauroyl sarcosinate, as a second anionic surfactant sodium laureth sulfate with 1-5 ethoxylate units, and as amphoteric surfactant a lauryl hydroxysultaine, and the total concentration of the aforementioned surfactants is in the range from 6% to 18% by weight, preferably from 7% to 18% by weight, more preferably from 8% to 18% by weight, calculated to the total of the composition.

In the most preferred embodiment, the first anionic surfactant is sodium laureth sulfate with 1-5 ethoxylate units, the second anionic surfactant is sodium lauroyl sarcosinate, the amphoteric surfactant is sodium lauryl hydroxysultaine, and the composition further comprises ethylhexyl glycerin.

The composition may further comprise cationic surfactants of quaternary ammonium structure according to

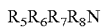

wherein $R_5$ is an alky chain having C length of 8 to 30 which may be saturated or unsaturated, straight or branched, $R_6$ is an alkyl chain having C length of 1 to 30 which may be saturated or unsaturated, straight or branched, $R_5$ and $R_6$ additionally may take the structures of

wherein $R_9$ is an alkyl chain with a C length of 7 to 29 which may be saturated or unsaturated, straight or branched and n1 is a number between 1 and 4, $R_7$ and $R_8$ are same or the different alkyl chain with a C length of 1 to 4 which may be straight or branched (only for $C_3$ and $C_4$), wherein all alkyl chains may comprise one or more substituents such as hydroxyl- or (poly)-ethoxy groups.

The concentration of cationic surfactants is in the range of 0.1% to 10% by weight, preferably 0.5% to 7.5% by weight, more preferably 1% to 5% by weight, calculated to the total of the composition.

Anions for the cationic surfactants may be selected from chloride, sulfate, or nitrate.

The composition may further comprise linear and/or cyclic non-aminated silicones and/or non-aminated siliconols.

Suitable non-aminated silicones and/or non-aminated siliconols are dimethicone, dimethiconol, polydimethylsiloxane (DC fluid ranges from Dow Corning), arylated silicones such as phenyl methicone, phenyl trimethicone, diphenyl dimethicone, diphenylsiloxy phenyl trimethicone, tetramethyl tetraphenyl trisiloxane, triphenyl trimethicone, and trimethyl pentaphenyl trisiloxane, aqueous emulsions of divinyldimethicone/dimethicone copolymer, preferably with a viscosity of higher than $1\times10^8$ mm$^2$/s, more preferably higher than $1.1\times10^8$ mm$^2$/s measured at 0.01 Hz and at approximately 25° C.

In a particular embodiment of the present invention, the concentration of non-aminated cyclic silicones and/or non-aminated linear silicones is in the range from 1% to 30% by weight, preferably from 2% to 25% by weight, more preferably in the range from 5% to 25% by weight, calculated to the total of the composition.

The composition may further comprise aminosilicone(s) which is/are not in the form of a microemulsion, preferably selected from a. a compound according to the general structure

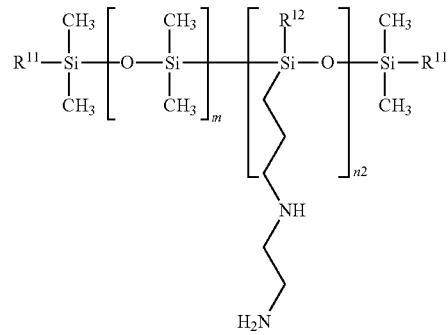

Wherein $R^{11}$ is selected from OH, OCH$_3$, and/or O—Si—(CH$_3$)$_3$, $R^{12}$ is selected from CH$_3$, OCH$_3$, O—(Si—(CH$_3$)$_2$)x-R$^{13}$, and/or O—Si—(CH$_3$)$_3$, with the provision that if $R^{11}$ or $R^{12}$ are selected from O—Si—(CH$_3$)$_3$, then all other $R^{12}$ or $R^{13}$ are selected from O—Si—(CH$_3$)$_3$ and/or OCH$_3$. M and n2 are numbers independently of each other and in the range of 1 to 200. Special special reference is made to the aminosilicones sold by Wacker Corporation under the trade name Belsil ADM 652 and Belsil ADM 653, and the ones sold by by Shin-Etsu Corp. under the trade name X-52-2265.

b. silicone graft copolymer comprising an organopolysiloxane segment as a main chain thereof and an unsaturated monomer-derived polymer segment as a side chain thereof, which is obtainable by firstly reacting an aminopropyl dimethicone with the thiolactone of acetyl homocysteine and then graft copolymerizing the thus obtained mercapto modified dimethicone with a mixture of N,Ndimethylacrylamide and N-t-butylacrylamide. Such a polymer is known under the CTFA name Polysilicone 28 and marketed by Kao Corporation.

c. an organopolysiloxane, wherein at least two silicon atoms in an organopolysiloxane segments constituting a main chain of the organopolysiloxane are bound to poly(N-acylalkyleneimine) segments consisting of repeating units represented by the following general formula via alkylene group containing hetero atom:

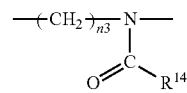

wherein $R^{14}$ is a hydrogen atom, an alkyl group having 1 to 22 carbon atoms, an aralkyl group, or an aryl group; and n3 is 2 or 3; wherein the number-average molecular weight of the poly-(N-acylalkyleneimine) segment is from 1,200 to 5,500, wherein the weight ratio of the organopolysiloxane segments (a) constituting the main chain to the poly-(N-acylalkyleneimine) segments (b) i.e., a/b is from 35/65 to 60/40, wherein the weight-average molecular weight of the adjacent poly-(N-acylalkyleneimine) segments is from 1,300 to 5,500, and wherein the weight-average molecular weight of the organopolysiloxane segment constituting the main chain is from 7,000 to 100,000. Such a polymer is known under the CTFA name Polysilicone 9 and marketed by Kao Corporation. Derivatives of this polymer are disclosed in EP2502615 which is referenced herein.

The total concentration of aminosilicone(s) which are not in the form of a microemulsion is/are in the range from 0.1% to 5% by weight, preferably from 0.2% to 4% by weight, and more preferably from 0.25% to 2.5% by weight, calculated as active matter to the total of the composition.

The composition may comprise one or more inorganic, monovalent salt(s) as a first thickening agent wherein the preferred salt is sodium chloride, and PEGylated or non-PEGylated esters of $C_{12}$ to $C_{18}$ fatty acids with pentaerythritol as a second thickening agent.

The viscosity of the composition of the present invention may be adjusted by thickening agents and should not exceed more than 30,000 mPas at 20° C. measured with Brookfield Rheometer at a shear rate of 5 $sec^{-1}$. Preferably the viscosity of the composition is in the range of 5,000 mPas to 25,000 mPas, more preferably 5,000 mPas to 20,000 mPas, each measured at 20° C. with Brookfield Rheometer at a shear rate of 5 $sec^{-1}$.

The composition comprises inorganic, monovalent salt(s) at a concentration in the range from 0.1% to 3.0% by weight, preferably from 0.2% to 2.5% by weight, more preferably from 0.5% to 2.0% by weight, calculated to the total of the composition.

The second thickening agent is PEGylated or non-PEGylated esters of $C_{12}$ to $C_{18}$ fatty acids with pentaerythritol. The preferred compound is PEG-150 pentaerythrityl tetrastearate.

Further suitable thickening agents may be nonionic thickening polymers. Suitable non-limiting examples are cellulose derivatives such as hydroxyethyl cellulose, methyl cellulose, hydroxymethyl cellulose, hydroxypropyl cellulose, guar gum and its derivatives, and konjac mannan and derivatives. Such Thickeners may be included at a concentration of 0.05 to 2.5% by weight calculated to total composition. Concentration of thickener is very much dependent on the thickener itself and also the preparation such as pH value of the composition etc. and therefore should be selected depending on the desired viscosity of the composition.

In a particular embodiment of the present invention, the composition of the present invention is transparent when being judged with the naked eye by an observer through a layer thickness of 1 cm. However, the composition may be colored with dyestuffs.

The composition according to the present invention may comprise one or more dyestuffs wherein the dyestuffs are selected from non-ionic, nitro, cationic and/or anionic direct dyes.

Suitable anionic direct dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the most preferred anionic dyestuffs are Acid Red 52, DC Violet 2, DC Red 33, DC Orange 4, DC Red 27, DC Yellow 10, HC Blue 18, HC Red 18, and HC Yellow 16.

Suitable cationic dyes are in principle those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87, HC Blue 17 and Basic Orange 31. The most preferred ones are Basic red 51, Basic Yellow 87 and Basic Orange 31 sold by BASF, HC Blue 17, Basic Blue 124.

Suitable neutral dyes including nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

The composition may comprise one or more hair direct dye at a total concentration of 0.001% to 10% by weight, preferably 0.005% to 7.5% by weight, and more preferably 0.01% to 5% by weight, calculated to the total of the composition. The composition can also comprise a mixture of several direct dyes, i.e., an anionic, a cationic and/or nonionic ones. In such a case the dyes may be mixed at any ratio with each other.

The pH of the compositions according to the present invention is suitably between 3.0 and 8.0 and preferably in the range of 3.5 to 6.5, more preferably 4.5 to 6.0 and most preferably 4.5 to 5.5.

In principle, the pH of the composition can be adjusted with any organic and/or inorganic acid(s) or base or their mixtures. Suitable acids are phosphoric acid, hydrochloric acid as the inorganic ones and to the organic acids the well-known citric acid and lactic acid, glycolic acid, glyoxylic acid, hydroxyacrylic acid, glyceric acid, malic acid and tartaric acid and of the dicarboxylic acids are malonic acid, succinic acid, glutaric acid, adipic acid, maleic acid, fumaric acid and phtalic acid. Suitable bases are sodium hydroxide or potassium hydroxide.

The composition of the present invention may additionally comprise any compound customarily found in cleansing compositions such as chelating agents, preservatives and fragrance.

Suitable chelating agents are selected from polycarboxylic acids. The preferred one is ethylene diamine tetraacetic acid, i.e. EDTA. A typical useful concentration range for chelating agents is 0.01% to 2.5% by weight, calculated to the total composition.

The composition of the present invention may comprise one or more organic solvents. Suitable organic solvents are ethanol, propanol, isopropanol, benzyl alcohol, benzyloxyethanol, ethoxydiglycol, alkylene carbonates such as ethylene carbonate and propylene carbonate, phenoxyethanol, butanol, isobutanol, cyclohexane, cyclohexanol, butylene glycol, ethylenecarbonate, propyleneglycol, polypropylene glycols, ethyleneglycol monoethylether, ethylene glycol monobutyl ether, ethylene glycol monophenyl ether, 1-phenylethylalcohol, 2-phenylethylalcohol, o-methoxyphenol.

The most preferred ones are butylene glycol, ethanol, isopropanol, benzylalcohol and polypropylene glycols.

The concentration of organic solvents should not exceed 10%, and preferably range from 0.1% to 7.5% by weight, more preferably from 0.1% to 5% by weight, calculated to the total of the composition.

The skilled in the art will recognize that the majority of the aforementioned organic solvents may act as preservatives as well. However, the composition of the present invention may comprise any other known preservative or preservative mixture besides and/or including organic solvents.

The composition of the present invention may further comprise cationic conditioning polymers. Suitable cationic polymers are those of best known with their INCI category name Polyquaternium.

Typical examples of those are Polyquaternium 1, Polyquaternium 2, Polyquaternium 4, Polyquaternium 5, Polyquaternium 6, Polyquaternium 7, Polyquaternium 8, Polyquaternium 9, Polyquaternium 10, Polyquaternium 11, Polyquaternium 12, Polyquaternium 13, Polyquaternium 14, Polyquaternium 15, Polyquaternium 16, Polyquaternium 17, Polyquaternium 18, Polyquaternium 19, Polyquaternium 20, Polyquaternium 22, Polyquaternium 24, Polyquaternium 27, Polyquaternium 28, Polyquaternium 29, Polyquaternium 30, Polyquaternium 31, Polyquaternium 32, Polyquaternium 33, Polyquaternium 34, Polyquaternium 35 and Polyquaternium 36, Polyquaternium-37, Polyquaternium 39, Polyquaternium 42, Polyquaternium 43, Polyquaternium 44, Polyquaternium 45, Polyquaternium 46, Polyquaternium 47, Polyquaternium 48, Polyquaternium 49, Polyquaternium 50, Polyquaternium 51, Polyquaternium 52, Polyquaternium 53, Polyquaternium 54, Polyquaternium 55, Polyquaternium 56, Polyquaternium 57, Polyquaternium 58, Polyquaternium 59, Polyquaternium 60, Polyquaternium 61, Polyquaternium 62, Polyquaternium 63, Polyquaternium 64, Polyquaternium 65, Polyquaternium 66, Polyquaternium 67, Polyquaternium 68, Polyquaternium 69, Polyquaternium-70, Polyquaternium 71, Polyquaternium 72, Polyquaternium 73, Polyquaternium 74, Polyquaternium 75, Polyquaternium 76, Polyquaternium 77, Polyquaternium 78, Polyquaternium-79, Polyquaternium 80, Polyquaternium 81, Polyquaternium 82, Polyquaternium 83, Polyquaternium 84, Polyquaternium 85, Polyquaternium 86 and Polyquaternium 87 as well as silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20, silicone quaternium-21 and silicone quaternium-22.

As well those polymers known with their INCI category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

It has further been found out that especially those of cationic cellulose type polymers known as Polymer JR type from Amerchol such as Polyquaternium 10 or cationic galactomannans such as cationic guar gum known with trade name Jaguar from Rhône-Poulenc which are chemically for example Guar hydroxypropyl trimonium chloride and cationic tarn gum and its derivatives known with INCI name Caesalpinia spinosa hydroxypropyltrimonium chloride, are preferred ones. Furthermore, chitosan and chitin can also be included in the compositions as cationic natural polymers. In this context reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The most preferred cationic polymers are those of cationic cellulose derivatives, cationic guar gum derivatives, cationic Caesalpinia spinosa gum derivatives, polyquarternium 6, polyquarternium 7, polyquarternium 10, polyquarternium 37, polyquarternium 67 and polyquarternium 70.

The cationic polymers also include the quaternized products of graft polymers from organopolysiloxanes and polyethyl oxazolines described in EP-A 524 612 and EP-A 640 643.

Compositions comprise cationic polymer at a concentration of 0.01 to 5%, preferably 0.02 to 4%, more preferably 0.05 to 3% and most preferably 0.1 to 2.5% by weight, calculated to the total of the composition.

The composition of the present invention may further comprise one or more UV filters which may be selected from water soluble ones as well as oils soluble ones. The oil soluble UV filter are more preferred ones as they show no interaction with the cationic quaternary ammonium polymers. Non-limiting examples are 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxy-benzophenone, 2-hydroxy-4-methoxybenzophenone and its 5-sulfonic acid or the sodium salt thereof, 2.2'-dihydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof, 3-(4'-methyl benzylidene)-DL-campher, and/or polysilicone-15.

The total UV filter concentration may be in the range of 0.01% to 1% by weight, calculated to the total composition.

In a further embodiment of the present invention, the composition may comprise one or more ubiquinone derivatives of the following general structure

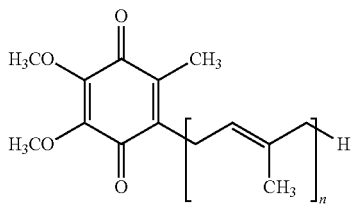

where n is a number between 1 and 10. It should be noted that the compositions of the present invention can certainly comprise more than one ubiquinone. Preferred ubiquinones are the ones where n is a number between 6 and 10 and especially preferred is Ubiquinone 50 where n is 10, also known as Coenzyme Q10.

The composition may further comprise one or more amino acid(s). Suitable amino acids may be all of the known amino acids such as arginine, alanine, asparagine, glutamine, glycine, histidine, leucine, lysine, methionine, phenylalanine, proline, serine, threonine, tryptophan, tyrosine and valine.

The composition may further comprise a compound according to the general structure

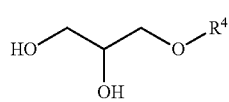

Formula V wherein $R^4$ is a linear or branched alkyl chain with a total carbon number of $C_3$ to $C_{12}$, preferably $C_3$ to $C_8$, more preferably $R^4$ is a branched alkyl chain with a total carbon number of $C_8$.

Suitable compounds are propyl glycerine, butyl glycerine, pentyl glycerine, hexyl glycerine, heptyl glycerine, octyl glycerine, nonyl glycerine, decyl glycerine, undecyl glycerine, dodecyl glycerin, ethylhexyl glycerine.

The preferred compound is ethylhexyl glycerine.

The composition may comprise the compound according to Formula V at a concentration in the range of 0.1% to 1% by weight, preferably from 0.2% to 1% by weight, more preferably from 0.25% to 1% by weight, calculated to the total of the composition.

The concentration of amino acids may be in the range of 0.01% to 5% by weight, preferably 0.1% to 3% by weight, and more preferably 0.2% to 2.5% by weight, and most preferably 0.25% to 2% by weight, calculated to the total of the composition.

The composition of the present invention may further comprise any known vitamin and/or antioxidant.

The following examples are to illustrate the present invention, but not to limit it.

EXAMPLE 1

The compositions 1-4 below were prepared by conventional dissolution and mixing techniques and the pH was set to 5.0 for all compositions.

| INCI | Comparative | Inventive |
| --- | --- | --- |
| Amodimethicone microemulsion* | — | 0.1% |
| Amodimethicone** | 0.1% | — |
| Octyldodecyl PCA*** | 0.5% | 0.5% |
| Sodium PCA**** | 0.5% | 0.5% |
| Water | Ad 100% | |

*DC CE 8170 AF
**DC 2-8566
***Sebumol ODPC
****Protelan PCA 40

Human hair streaks (21 cm long, approximately 2 g per streak) were obtained from Fischbach & Miller, Laupheim, Germany. Hair streaks were permed with compositions available under the Goldwell Structure+Shine brand, and colored with oxidative hair color available under the brand Goldwell Topchic. To the permed and colored hair streaks 1 g of the compositions was applied and massaged into the hair streak for 60 s. The streaks were then rinsed-off with water and blow-dried. A test panel consisting of 10 trained experts dealing with hair cosmetics and hair fibers every day evaluated the hair streaks. The panelist evaluation was performed under standardized conditions (humidity, temperature, light box) and the experts were not informed on the treatment prior to their evaluation. Experts were asked to grade color brilliance wherein values from 1-10 possible were possible and 10 was the highest score. For statistical evaluation, the scores were then assessed with a t-test. A value of $p<0.05$ was considered as statistically significant.

| Panelist | Comparative | Inventive |
| --- | --- | --- |
| 1 | 6 | 8 |
| 2 | 5 | 8 |
| 3 | 5 | 7 |
| 4 | 6 | 8 |
| 5 | 6 | 7 |
| 6 | 8 | 9 |
| 7 | 6 | 8 |
| 8 | 8 | 9 |
| 9 | 5 | 8 |
| 10 | 5 | 7 |
| Mean value | 6.0 | 7.5 |
| Standard deviation | 1.15 | 0.74 |
| t-test | $p < 0.01$ | |

As a result of above panel test, experts preferred the inventive composition significantly more than any of the comparative compositions in terms of color brilliance.

EXAMPLE 2

The same hair quality as outlined in example 1 was purchased. In contrast to example 1, the hair streaks were bleached with commercial bleach available under the brand name Goldwell SilkLift Control, and then colored with an oxidative color available under the trade name Goldwell Topchic. The hair streaks were treated with the the compositions of example 1 and processed accordingly. Color intensity was measured photometrically in the Lab color space and ΔE values were calculated according to the well-known equation. The hair streaks were then washed in a waterbath filled with an aqueous solution of 5% by weight of sodium laureth sulphate. The streaks were allowed to be immersed for 60 s under mild shaking (30 rpm). The streaks were blow-dried prior to photometric measurements. The washing cycles were repeated for 2, 4, 9, and 19 more times.

The table below reports the measured ΔE values in comparison to the unwashed hair streak. The lower the values the better the wash fastness/remaining color intensity.

| Washing cycle(s) | Comparative [ΔE] | Inventive [ΔE] |
|---|---|---|
| 1 | 3.16 | 2.10 |
| 3 | 3.35 | 2.15 |
| 5 | 3.25 | 2.25 |
| 10 | 4.22 | 2.88 |
| 20 | 5.33 | 2.63 |

As a result of the experiments, the inventive composition showed little change in ΔE directly upon the first washing step whereas the comparative example showed higher values. This observation was maintained over 20 washing cycles wherein the inventive composition exhibited the least loss in color intensity. Consequently, the inventive composition had the highest wash fastness on bleached and colored hair.

EXAMPLE 3

The hair streak preparation of example 1 was repeated and the compositions were consequently applied onto permed and colored hair. The wash fastness test of example 2 with identical methodology was applied. The ΔE results are reported in the table below.

| Washing cycle(s) | Comparative [ΔE] | Inventive [ΔE] |
|---|---|---|
| 1 | 2.69 | 1.81 |
| 3 | 3.0 | 1.87 |
| 5 | 3.54 | 1.92 |
| 10 | 3.11 | 1.95 |
| 20 | 3.99 | 1.96 |

The trend of the superiority of the inventive composition was confirmed on permed and colored hair. Upon the first washing step, the inventive composition had much lower ΔE value in comparison to the comparative composition. Moreover, the trend of lower ΔE values for the inventive composition over the 20 washing cycles was confirmed in this experiment as well, resulting upon 20 washing cycles in about half of the comparative composition. Thus, the inventive composition exhibited better wash fastness in comparison to all comparative compositions on permed and colored hair as well.

The following examples are within the scope of the invention.

EXAMPLE 4

A cleansing composition with the following composition:

| | % by weight |
|---|---|
| Sodium laureth sulfate | 11.0 |
| Sodium lauroyl sarcosinate | 3.0 |
| Lauryl hydroxysultaine | 1.0 |
| Ethylhexylglycerin | 0.75 |
| Decyl glycoside | 1.0 |
| Sodium chloride | 1.0 |
| PEG-150 pentaerythrityl tetrastearate | 0.15 |
| Amodimethicone microemulsion* | 0.02 |
| Octyldodecyl PCA | 0.05 |
| Sodium PCA | 0.1 |
| Polyquaternium 10 | 0.3 |
| Lactic acid | q.s. to pH 5.5 |
| HC Blue 17 | 0.1 |
| Water | ad 100.0 |

*X-52-2265 sold by Shin-Etsu Corp.

EXAMPLE 5

A leave-in composition according to the following formula was prepared:

| | % by weight |
|---|---|
| Trisiloxane | 14 |
| Cyclopentasiloxane | 10 |
| Dimethiconol | 2 |
| Phenyl Trimethicone | 1.5 |
| Polyquaternium 37 | 1.1 |
| Phenoxyethanol | 0.6 |
| Amodimethicone microemulsion* | 0.6 |
| Octyldodecyl PCA | 0.1 |
| Glycoproteins | 0.002 |
| Sodium PCA | 0.1 |
| Citric Acid | q.s. to pH 4 |
| Basic Red 51 | 0.05 |
| Water | ad 100.0 |

*DC CE 8170 AF sold by Dow Corning

EXAMPLE 6

A cleansing composition with the following composition:

| | % by weight |
|---|---|
| Sodium laureth sulfate | 11.0 |
| Sodium lauroyl sarcosinate | 3.0 |
| Lauryl hydroxysultaine | 1.0 |
| Decyl glycoside | 0.8 |
| Ethylhexylglycerin | 0.75 |
| Sodium chloride | 1.0 |
| PEG-150 pentaerythrityl tetrastearate | 0.15 |
| Amodimethicone microemulsion* | 0.02 |
| Octyldodecyl PCA | 0.05 |
| Octyl PCA | 0.05 |
| Potassium PCA | 0.1 |
| Sodium PCA | 0.1 |
| Polyquaternium 10 | 0.3 |
| Basic Red 51 | 0.05 |
| Lactic acid | q.s. to pH 5.2 |
| Water | ad 100.0 |

*DC CE 8170 AF sold by Dow Corning

The invention claimed is:

1. An aqueous cosmetic composition comprising:
a) at least one compound according to the general structure

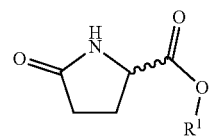

wherein R1 is selected from straight, saturated, or unsaturated alkyl chain between C12 and C20 or branched, saturated or unsaturated alkyl chain with C12 to C20;
b) pyrrolidone carboxylic acid and/or its salt; and
c) amodimethicone in the form of a microemulsion wherein the microemulsion of amodimethicone is an emulsion with a droplet size in the range of 50 nm to 1000 nm.

2. The aqueous cosmetic composition of claim 1, wherein the at least one compound a) is octyldodecyl pyrrolidone carboxylic acid.

3. The aqueous cosmetic composition of claim 1, wherein the aqueous cosmetic composition further comprises glycoproteins and/or hydrolyzed glycoproteins.

4. The aqueous cosmetic composition of claim 3, wherein a total concentration of glycoproteins and/or their hydrolyzates in the aqueous cosmetic composition ranges from 0.001% to 2% by weight, calculated as dry matter to a total of the aqueous cosmetic composition.

5. The aqueous cosmetic composition of claim 1, wherein a weight ratio of a) and b) is in the range of 0.1 to 100.

6. The aqueous cosmetic composition of claim 1, wherein the amodimethicone is present at a concentration range from 0.001% to 1% by weight, calculated as active amodimethicone matter to a total of the aqueous cosmetic composition.

7. The aqueous cosmetic composition of claim 1, further comprising one or more anionic surfactant at a total concentration in a range of 6% to 18% by weight, calculated to a total of the aqueous cosmetic composition.

8. The aqueous cosmetic composition of claim 1, wherein a pH of the aqueous cosmetic composition is in the range of 2 to 7.

9. The aqueous cosmetic composition of claim 1, further comprising at least one of one or more non-aminated cyclic silicones and one or more non-aminated linear silicones at a concentration in the range of 1% to 30% by weight, calculated to a total of the aqueous cosmetic composition.

10. The aqueous cosmetic composition of claim 1, further comprising at least one of one or more amphoteric surfactants and one or more zwitterionic surfactants at a total concentration ranging from 0.1% to 2%, calculated to a total of the aqueous cosmetic composition.

11. The aqueous cosmetic composition of claim 1, further comprising one or more non-ionic surfactants.

12. The aqueous cosmetic composition of claim 1, further comprising or more hair direct dyes selected from non-ionic, nitro, cationic, and anionic direct dyes.

13. A process for maintaining color brilliance and shine, and improving wash fastness of artificially colored keratin fibers, the process comprising:
a) optionally wetting and/or cleansing the hair;
b) applying the aqueous cosmetic composition of claim 1 onto the hair and massaging it into keratin fibers for 10 seconds to 600 seconds;
c) optionally rinsing the aqueous cosmetic composition off the hair;
d) optionally drying the hair.

* * * * *